US008457981B2

(12) United States Patent
Schoenberg (10) Patent No.: US 8,457,981 B2
(45) Date of Patent: Jun. 4, 2013

(54) BRIDGED PATIENT / PROVIDER CENTRIC METHOD AND SYSTEM

(75) Inventor: Roy Schoenberg, Boston, MA (US)

(73) Assignee: The TriZetto Group, Inc., Greenwood Village, CO (US)

(*) Notice: Subject to any disclaimer, the term of this patent is extended or adjusted under 35 U.S.C. 154(b) by 3837 days.

(21) Appl. No.: 10/726,423

(22) Filed: Dec. 3, 2003

(65) Prior Publication Data
US 2005/0125252 A1 Jun. 9, 2005

(51) Int. Cl.
*G06Q 10/00* (2012.01)
*G06Q 50/00* (2012.01)

(52) U.S. Cl.
USPC .............................................................. 705/2

(58) Field of Classification Search
None
See application file for complete search history.

(56) References Cited

U.S. PATENT DOCUMENTS

| | | | |
|---|---|---|---|
| 4,882,474 A | 11/1989 | Anderi et al. | 235/380 |
| 5,704,044 A | 12/1997 | Tarter et al. | 395/204 |
| 5,805,719 A | 9/1998 | Pare, Jr. et al. | 382/115 |
| 6,076,166 A | 6/2000 | Moshfeghi et al. | 713/201 |
| 6,463,417 B1 | 10/2002 | Schoenberg | 705/2 |
| 6,941,271 B1* | 9/2005 | Soong | 705/3 |

FOREIGN PATENT DOCUMENTS
WO    WO01/26020 A1    4/2001

OTHER PUBLICATIONS

Annas, G., "A National Bill of Patient's Rights", NEJM, 338, p. 695-699, Mar. 5, 1998.
Bakker, A., "Security in Perspective; Luxury or Must?", Int. J. Med. Inf., 49, p. 31-37, 1998.
Baker, D., "PCASSO: Providing Secure Internet Access to Patient Information", www.saic.com.
Barrows, R. Jr. et al., "Privacy, Confidentiality, and Electronic Medical Records", J. Amer. Med. Inf. Assoc., 3, p. 139-148, Mar. 1996.
Cimino, J. et al., "Architecture for a Web-Based Clinical Information System that Keeps the Design Open and the Access Closed", Proc. AMIA Symp., p. 121-125, 1998.
Dudeck, J., "Aspects of Implementing and Harmonizing Healthcare Communication Standards", Int. J. Med. Inf., 48, p. 163-171, Feb. 1998.
Epstein, M. et al., "Security for the Digital Information Age of Medicine: Issues, Applications, and Implementation", J. Digit Imaging, 11, p. 33-44, Feb. 1998.
Espinosa, A., "Availability of Health Data: Requirements and Solutions", Int. J. Med. Inf., 49, p. 97-104, Mar. 1998.
Gibby, G. et al., "Availability of Records in An Outpatient Preanesthetic Evaluation Clinic", J. Clin. Mon. & Computing, 14, p. 385-391, Aug. 1998.
Kuilboer, M. et al., "The Availability of Unavailable Information", AMIA Annual Fall Symp., p. 749-753, 1997.
Leape, L., "Error in Medicine", JAMA, 272, p. 1851-1857, Dec. 21, 1994.
Leape, L. et al., "Promoting Patient Safety by Preventing Medical Error", JAMA, 280, p. 1444-1447, Oct. 28, 1998.

(Continued)

*Primary Examiner* — Sheetal R Rangrej
(74) *Attorney, Agent, or Firm* — Dawn-Marie Bey; King & Spalding LLP (57) ABSTRACT

A key organization method and system includes receiving a first access key that grants a patient-defined level of access to a first set of medical records, receiving a second access key that grants a patient-defined level of access to a second set of medical records, and storing the first and second access keys in a centralized key repository.

39 Claims, 6 Drawing Sheets

OTHER PUBLICATIONS

Luxenberg, S. et al., "Electronic Forms: Benefits and Drawbacks of A World Wide Web-Based Approach to Data Entry", Proc. AMIA Annual Fall Symp., p. 804-808, 1997.

Mandl, K. et al., "Electronic Patient-Physician Communication: Problems and Promise", Ann. Intern. Med., 129, p. 495-500, Sep. 15, 1998.

Masys, D. et al., "Patient-Centered Access to Secure Systems Online (PCASSO): A Secure Approach to Clinical Data Access Via the World Wide Web", Proc. AMIA Annual Fall Symp., p. 340-343, 1997.

Auston, I. Et al., "Confidentiality of Electronic Health Data: Methods for Protecting Personally Identifiable Information", National Library of Medicine, CBM 95-100, Mar. 1996.

Neame, R., "Smart Cards—The Key to Trustworthy Health Information Systems", BMJ, 314, p. 573-577, Feb. 22, 1997.

Rind, D. et al., "Maintaining the Confidentiality of Medical Records Shared Over the Internet and the World Wide Web", Ann. Intern. Med., 127, p. 138-141, Jul. 15, 1997.

Schoenberg. R. et al., "Internet Based Repository of Medical Records that Retains Patient Confidentiality", BMJ, 321, p. 1199-1203, Nov. 11, 2000.

Slack, W. et al., "The CCC System in Two Teaching Hospitals: A Progress Report", Int. J. Med. Inf., 54, p. 183-196, Sep. 1999.

Stanberry, B., "The Legal and Ethical Aspects of Telemedicine 1: Confidentiality and the Patient's Rights of Access", J. Telemed. Telecare, 3, p. 179-187, 1997.

Toyada, K., "Standardization and Security for the EMR", Int. J. Med. Inf., 48, p. 57-60, Feb. 1998.

Woodward, B., "The Computer-Based Patient Record and Confidentiality", NEJM, 333, p. 1419-1422, Nov. 23, 1995.

Bell Atlantic and EMX Team Up to Provide Doctors Instant Online Access to Medical Data, PR Newswire, Feb. 23, 1999.

* cited by examiner

BRIDGED PATIENT / PROVIDER CENTRIC METHOD AND SYSTEM

RELATED APPLICATIONS

The following U.S. patent is hereby incorporated by reference into the subject application as if set forth herein in full: (1) U.S. Pat. No. 6,463,417, entitled "Method of Distributing Health Information".

FIELD OF THE INVENTION

This invention relates to medical record access control systems, and, more particularly, medical record access control systems that regulate the access-level granted to individual medical service providers.

BACKGROUND

The ability of a patient to regulate the access that a third party has to the patient's medical records has become a hotly-contested topic. Typically, systems that provide the patient with the ability to control access to their medical records (e.g., patient-centric systems) are often administratively-cumbersome for medical service providers. Conversely, systems that are easily administered by medical services providers (e.g., provider-centric systems) compromise the ability of a patient to control access to their medical records.

For patient-centric systems, the patient exclusively controls access to their health care records. Since the patient's healthcare records are centralized and stored in a single location, any provider that accesses the patient's medical record is going to see a complete and current medical record, as all the medical service providers access and amend the same record set.

While the patient-centric system is preferred by patients, it is difficult to implement, since it is often desirable to provide varying levels of access to different medical service providers. Therefore, each medical service provider typically requires a unique access key to gain access to each medical record. Accordingly, this system requires a considerable amount of administrative overhead for medical service providers, in that a medical service provider is required to maintain a unique key for each medical record to which they have access.

For provider-centric systems, the medical service provider maintains a medical record for each patient to which he provides service. Since the medical service provider creates and maintains these medical records, the medical service provider has unfettered access to the medical records. Further, as each of the medical records is not reconciled with the medical records maintained by other medical service providers for the same patient, each medical record represents only a partial record of a patient's medical history.

SUMMARY OF THE INVENTION

According to a first implementation, a key organization method includes receiving a first access key that grants a patient-defined level of access to a first set of medical records, receiving a second access key that grants a patient-defined level of access to a second set of medical records, and storing the first and second access keys in a centralized key repository.

One or more of the following features may also be included. The first access key may be generated by a first patient, and the first set of medical records may concern the first patient. The second access key may be generated by a second patient, and the second set of medical records may concern the second patient. A client computer connected to a distributed computing network may be used to access the first set of medical records using the first access key and/or the second set of medical records using the second access key. The client computer may be a personal computer, and the distributed computing network may be the Internet.

The first and second medical records may be stored on a centralized medical record repository. The centralized medical record repository and the centralized key repository may reside on and may be executed by a remote server connected to a distributed computing network. The remote server may be a web server, and the distributed computing network may be the Internet.

The first set of medical records may be a multi-portion medical record and the first access key may provide access to one or more portions of the first set of medical records. The second set of medical records may be a multi-portion medical record and the second access key may provide access to one or more portions of the second set of medical records.

According to a further implementation, a key distribution method includes: transmitting, from a first patient, a first access key that grants a patient-defined level of access to a first set of medical records; transmitting, from a second patient, a second access key that grants a patient-defined level of access to a second set of medical records; and storing the first and second access keys in a centralized key repository.

According to a further implementation, a key organization method includes: establishing, on a remote server, a centralized key repository and a centralized medical record repository; and storing a first set of medical records and a second set of medical records on the centralized medical record repository.

According to a further implementation, a key organization system includes: a server system including a computer processor and associated memory, the server system having a centralized key repository and a centralized medical record repository; such that the server system is configured to: store a first set of medical records and a second set of medical records on the centralized medical record repository; receive a first access key that grants a patient-defined level of access to the first set of medical records; receive a second access key that grants a patient-defined level of access to the second set of medical records; and store the first access key and the second access key on the centralized key repository.

One or more of the following features may also be included. A client system may include a computer processor and associated memory, the client system being configured to: access the first set of medical records using the first access key; and access the second set of medical records using the second access key. The server system and the client system may be coupled via a distributed computing network, such as the Internet.

According to a further implementation, a computer program product resides on a computer readable medium on which a plurality of instructions are stored. When executed by the processor, the instructions cause that processor to: receive a first access key that grants a patient-defined level of access to a first set of medical records; receive a second access key that grants a patient-defined level of access to a second set of medical records; and store the first and second access keys in a centralized key repository.

According to a further implementation, a computer program product resides on a computer readable medium on which a plurality of instructions are stored. When executed by the processor, the instructions cause that processor to: transmit, from a first patient, a first access key that grants a patient-defined level of access to a first set of medical records; transmit, from a second patient, a second access key that grants a patient-defined level of access to a second set of medical records; and store the first and second access keys in a centralized key repository.

According to a further implementation, a computer program product resides on a computer readable medium on which a plurality of instructions are stored. When executed by the processor, the instructions cause that processor to: maintain, on a remote server, a centralized key repository and a centralized medical record repository; and store a first set of medical records and a second set of medical records on the centralized medical record repository.

The details of one or more implementations are set forth in the accompanying drawings and the description below. Other features and advantages will become apparent from the description, the drawings, and the claims.

DETAILED DESCRIPTION OF THE PREFERRED EMBODIMENTS

Figure 1:
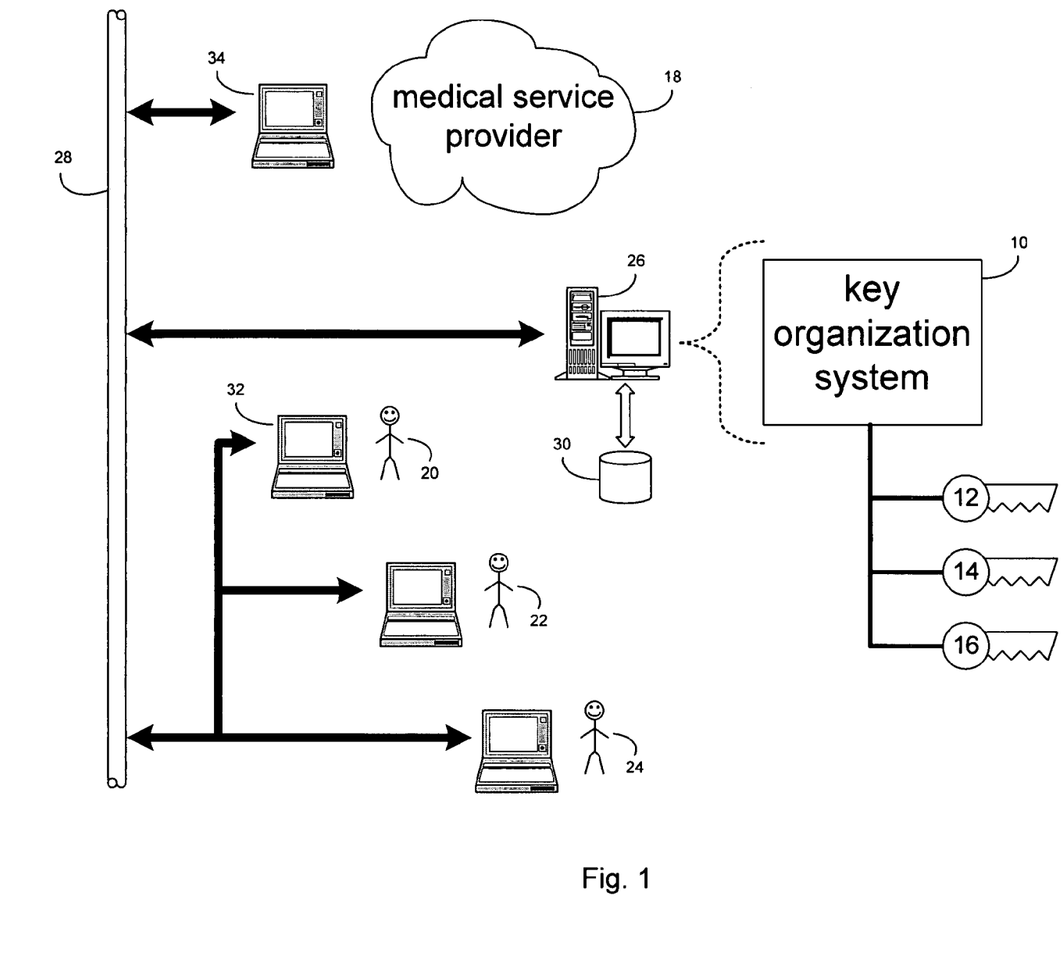
FIG. 1 is a diagrammatic view of key organization system coupled to a distributed computing network.

Referring to FIG. 1, there is shown a key organization system 10 that manages the various access keys 12, 14, 16 possessed by a medical service provider 18. Access keys 12, 14, 16 are provided to medical service provider 18 by various patients 20, 22, 24.

Key organization system 10 typically resides on and is executed by a computer 26 that is connected to network 28. Computer 26 may be a web server running a network operating system, such as Microsoft Window 2000 Server™, Novell Netware™, or Redhat Linux™. Typically, computer 26 also executes a web server application, such as Microsoft IIS™, Novell Webserver™, or Apache Webserver™, that allows for HTTP (i.e., HyperText Transfer Protocol) access to computer 26 via network 28.

The instruction sets and subroutines of key organization system 10, which are typically stored on a storage device 30 coupled to computer 26, are executed by one or more processors (not shown) and one or more memory architectures (not shown) incorporated into computer 26. Storage device 30 may be, for example, a hard disk drive, a tape drive, an optical drive, a RAID array, a random access memory (RAM), or a read-only memory (ROM).

As will be explained below in greater detail, a patient (e.g., patient 20) typically provides a key (e.g., access key 12) to medical service provider 18 through a patient computer 32, which is also connected to network 28. Additionally, medical service provider 18 accesses key organization system 10 through a client computer 34.

Figure 2:
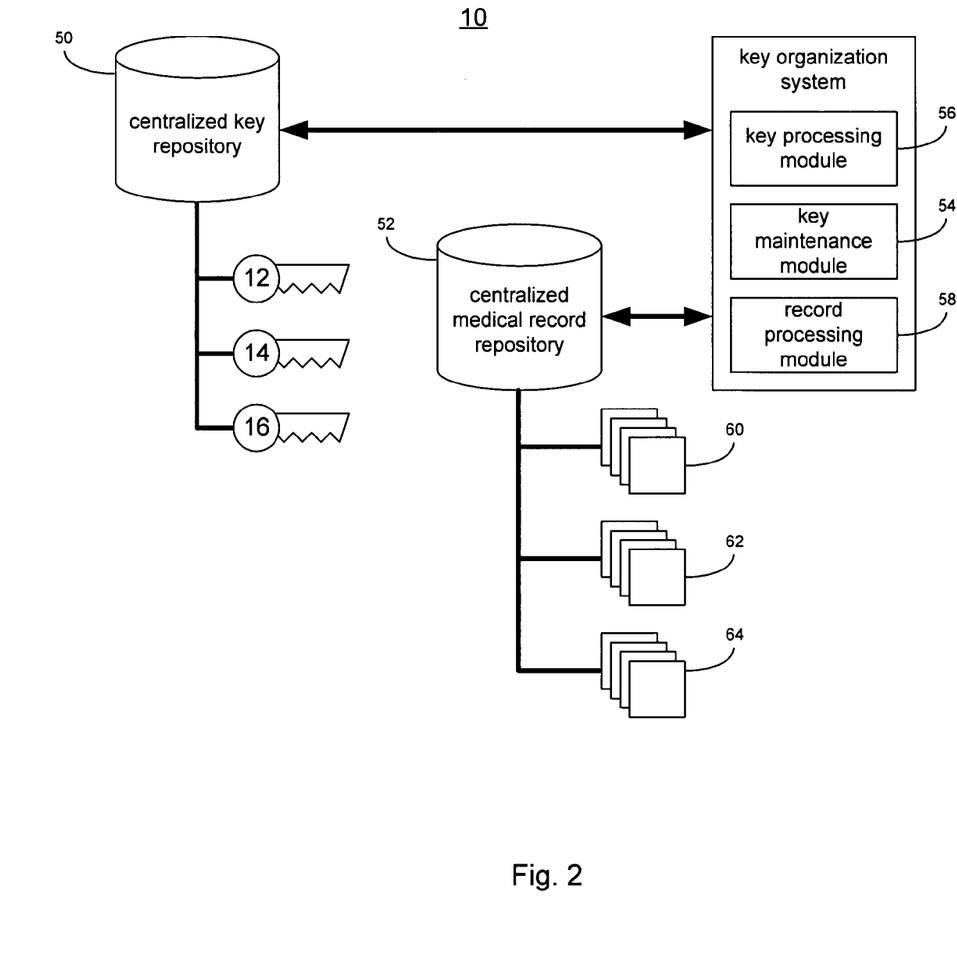
FIG. 2 is a more-detailed diagrammatic view of the key organization system of FIG. 1.

Referring also to FIG. 2, key organization system 10 includes a centralized key repository 50 and a centralized medical records repository 52. Additionally, key organization system 10 includes a key maintenance module 54, a key processing module 56, and a record processing module 58, each of which will be discussed below in greater detail.

Centralized medical records repository 52 allows for the centralized storage of medical records 60, 62, 64 concerning various patients 20, 22, 24 respectively. As disclosed in U.S. Pat. No. 6,463,417, medical records 60, 62, 64 are typically divided into portions or levels, in that certain portions are considered more confidential than other portions. For example, a portion/level of the medical record that may be considered the least confidential might include general patient identification information and information concerning the patient's blood type and allergies. A portion/level of a medical record that may be considered to have an intermediate level of confidentiality might include information concerning the serological data, psychiatric data, cardiology data, and genetic data. A portion/level of the medical record that may be considered highly confidential may include infectious disease (e.g., HIV, and sexually transmitted diseases) data.

This specific assignment of confidentiality levels and the apportionment of the medical record into various portions/levels is for illustrative purposes only and is not intended to limit the scope of this disclosure.

Medical records 60, 62, 64 may be incrementally generated/configured online by the various medical service providers that provide care to patients 20, 22, 24. Alternatively, existing medical records may be uploaded (i.e., transferred) to medical records repository 52 from a remote storage location (not shown).

Figure 3:
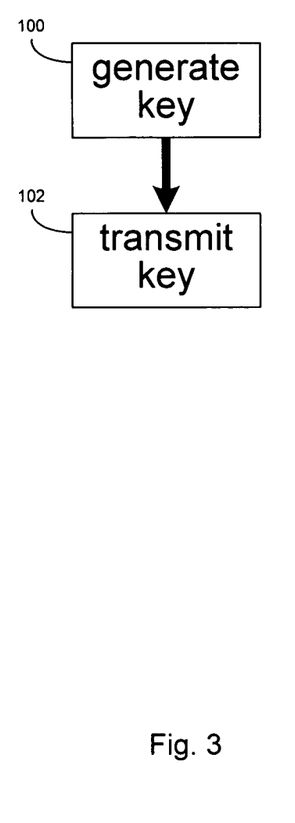
FIG. 3 is a block diagram of a key maintenance module of the key organization system of FIG. 1.

Referring also to FIG. 3, patients 20, 22, 24 use key maintenance module 54 to generate 100 access keys 12, 14, 16 that grant access to various portions of the respective medical records 60, 62, 64. Accordingly, though the use of key maintenance module 54, the patient can generate access keys that not only regulate who has access to their medical records, but also regulates the level of access (i.e., which portions of a patient's medical record are viewable by the medical service provider to which the key is provided). Examples of access keys 12, 14, 16 are passwords (that allow access to various portions of a medical record) and decryption keys (that decrypt various portions of an encrypted medical record).

Typically, key maintenance module 54 is a web-enabled application that is accessed by the patients (e.g., patient 20) through a browser application (e.g., Microsoft Internet Explorer™, or Netscape Navigator™) that is running on patient computer 32. Alternatively, key maintenance module 54 may be a local application that is executed locally on patient computer 32.

As stated above, key maintenance module 54 allows a patient to generate 100 an access key for a specific medical service provider that grants, to that medical service provider, a defined level of access to that patient's medical records. Once this access key is generated, the access key is transmitted 102 to the medical service provider 18. This transmission of the access key may be implemented by transferring the access key from the patient to the medical service provider. This may occur by attaching the access key to an email that is transmitted to the medical service provider. Once received, the medical service provider may then transfer the newly-generated key to the key processing module 56 (to be discussed below in greater detail) of the key organization system 10. Alternatively, the patient may directly transfer the newly-generated key to the key processing module 54 of the key organization system 10.

Figure 4:
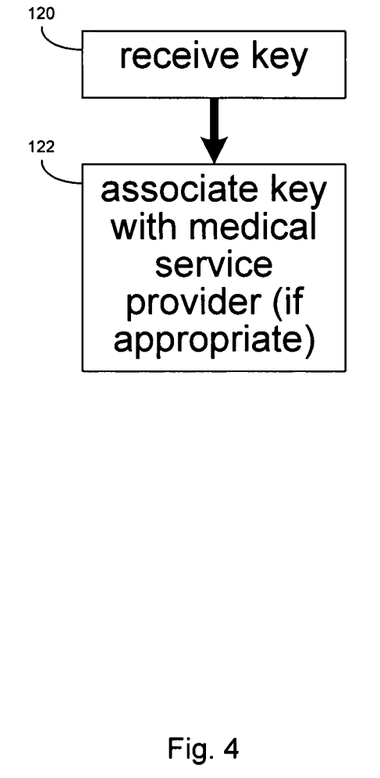
FIG. 4 is a block diagram of a key processing module of the key organization system of FIG. 1.

Now referring to FIGS. 1, 2 and 4, regardless of the manner in which the patient transfers the access key to the medical service provider, the access key will ultimately be received 120 by key processing module 56, which receives any access keys (e.g., keys 12, 14, 16) generated and transmitted by patients 20, 22, 24. Once these keys are received 120, they are stored 124 on centralized key repository 50. Additionally, if key organization system 10 is servicing multiple medical service providers (i.e., at least one medical service provider in addition to medical service provider 18), the received keys are associated 122 with the appropriate medical service provider so that the keys transmitted to a first provider are not available to a second provider.

Figure 5:
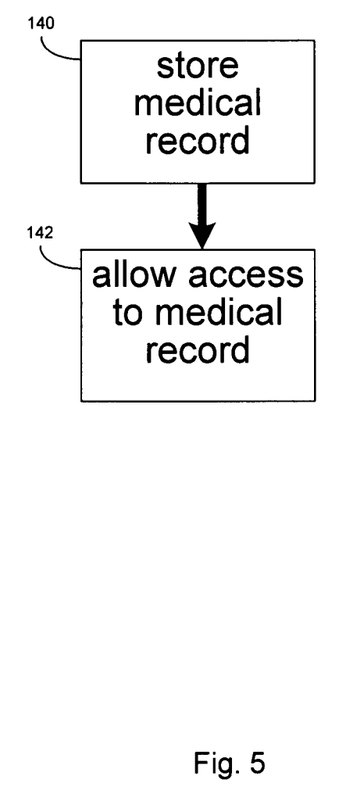
FIG. 5 is a block diagram of a record processing module of the key organization system of FIG. 1.

Now referring to FIGS. 1, 2 and 5, when medical records are initially received, initially generated, and/or edited, record processing module 58 stores 140 the medical record on centralized medical record repository 52. Typically, medical record repository 52 is a database that allows for the organized storage and retrieval of the medical records 60, 62, 64.

Once these medical records are stored on medical record repository 52, record processing module 58 allows the medical service provider 18 to access 142 the medical records 60, 62, 64 stored on medical records repository 52. However, the medical service provider 18 is only given access to the portions of the medical records for which the medical service provider 18 possesses the appropriate key. For example, assume that medical service provider 18 is a medical clinic that provides an array of medical services to its patients. Further, assume that patient 20 uses medical service provider 18 for all of their medical needs; patient 22 uses medical service provider 18 solely for treatment of depression; and patient 24 uses medical service provider 18 solely for treatment of HIV.

Concerning the access keys generated by each of these patients for medical service provider 18: patient 20 would typically provide medical service provider 18 with an access key (i.e., key 12) that grants access to their entire medical record; patient 22 would typically provide medical service provider 18 with an access key (i.e., key 14) that grants access to the general and psychiatric portions of their medical record; and patient 22 would typically provide medical service provider 18 with an access key (i.e., key 16) that grants access to the general and infectious disease portions of their medical record.

Record processing module 58 is typically a web-enabled application that is accessed by the medical service provider 18 through a browser application (e.g., Microsoft Internet Explorer™, or Netscape Navigator™) that is running on client computer 34. Typically, medical service provider 18 logs into key organization system 10 using an encrypted SSL (i.e., secure sockets layer) connection.

Figure 6:
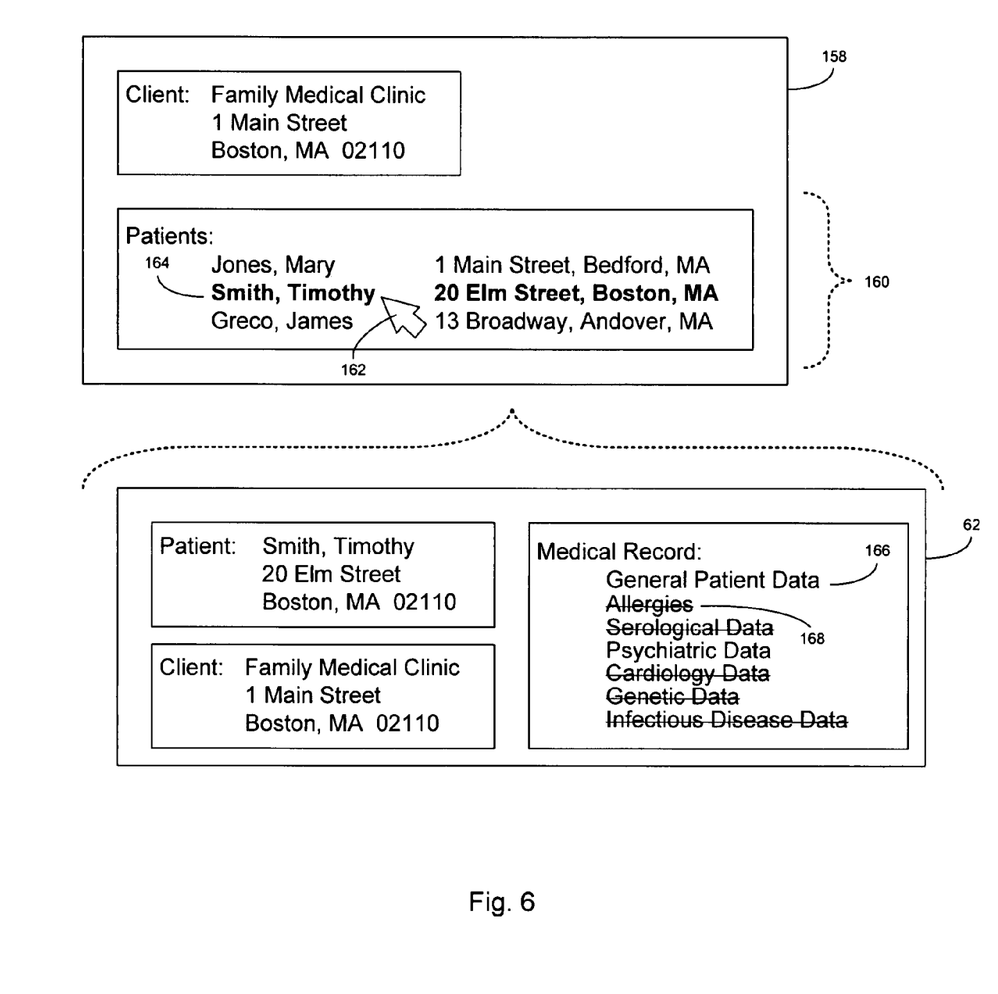
FIG. 6 is a diagrammatic view of a patient selection display screen rendered by the key organization system of FIG. 1.

Referring also to FIG. 6, when accessing key organization system 10, record processing module 58 provides the medical service provider 18 with a rendered screen display 158 that includes a list of patient identifiers 160. Patient identifiers 160 define the particular patient(s) who provided access keys to medical service provider 18 (i.e., granting medical service provider 18 access to various portions of their medical record (s)). The patient identifiers 160 may be any element that uniquely identifies the patient, such as the patient's name, the patient's social security number, or a unique patient number. In this particular example, Mary Jones is patient 20, Timothy Smith is patient 22, and James Greco is patient 24.

The presence of each of these names in the list of patient identifiers 160 indicates that a key was received from that patient. In order to access the medical record of a patient for which the medical service provider has a key (i.e., for one of the patients listed in the list of patient identifiers 160), the medical service provider 18 selects the appropriate identifier using a mouse pointer 162 (or some other pointing device, not shown). For example, if the medical service provider wanted to access the medical record of Timothy Smith (i.e., patient 22), medical service provider 18 would typically double click (using a mouse) on the specific identifier 164 associated with Timothy Smith. Record processing module 58 would then, in turn, use access key 14 to access (i.e., retrieve, decrypt, and display) medical record 62, the medical record of Timothy Smith, i.e., patient 22.

Medical record 62 may be displayed in a separate window or displayed full screen on the display of client computer 34. As discussed above, the key provided to the medical service provider 18 only allows access to the portion(s) of the patient's medical record that the patient wishes to allow access. As discussed above, Timothy Smith (i.e., patient 22) is being treated by medical service provider 18 for depression and access key 14 grants access to the general and psychiatric portions of Timothy Smith's medical record, such that a link (e.g., link 166) to each available portion is displayed on the right-hand side of medical record 64. However, access key 14 does not permit access (i.e., prohibits access) to the other portions of Timothy Smith's medical record, namely Allergies, Serological Data, Cardiology Data, Genetic Data, and Infectious Disease Data. Accordingly, the links (e.g., link 168) to the unavailable data portions are struck-through.

Other methods of differentiating the available portions from the unavailable portions of a medical record may be used, such as graying-out or not displaying links to the unavailable portions.

By clicking on the links to the available portions of the medical record, a specific available portion is displayed by record processing module 58.

While medical record 64 is shown to include a plurality of links to the available portions of the medical record, other configurations are possible. For example, when clicking on a specific identifier (e.g., identifier 164), a medical record may be displayed that only includes the portions to which the medical service provider has access.

While centralized key repository 50 is described above as being located on a remote server, other configurations are possible. For example, the centralized key repository may be stored locally on a computer operated by the medical service provider. Additionally, as is known in the art, a repository may be distributed across multiple computers/servers.

A number of implementations have been described. Nevertheless, it will be understood that various modifications may be made. Accordingly, other implementations are within the scope of the following claims.

What is claimed is:

1. A key organization method comprising:
receiving, by a key organization system operable on a computer processor, a first access key that grants, to a medical service provider, a patient-defined level of access to a first set of medical records;
receiving, by said key organization system, a second access key that grants, to said medical service provider, a patient-defined level of access to a second set of medical records;
storing the first and second access keys in a centralized key repository that is communicativalely accessible by said key organization system; and
associating, by said key organization system, said first and second access keys with said medical service provider.

2. The method of claim 1 wherein the first access key is generated by a first patient, and the first set of medical records concern the first patient.

3. The method of claim 1 wherein the second access key is generated by a second patient, and the second set of medical records concern the second patient.

4. The method of claim 1 further comprising controlling, by said key organization system, said medical service provider's access to the first set of medical records by allowing said medical service provider to select, from a list of patients for whom access keys are associated with said medical service provider, a corresponding patient to whom the first set of medical records pertains.

5. The method of claim 4 further comprising controlling, by said key organization system, said medical service provider's access to the second set of medical records by allowing said medical service provider to select, from said list of patients, a corresponding patient to whom the second set of medical records pertains.

6. The method of claim 4 wherein accessing the first set of medical records does not require said medical service provider to pass a second security test.

7. The method of claim 1 further comprising storing the first and second medical records on a centralized medical record repository.

8. The method of claim 7 wherein the centralized medical record repository and centralized key repository reside on and are executed by a remote server connected to a distributed computing network.

9. The method of claim 8 wherein:
the remote server is a web server; and
the distributed computing network is the Internet.

10. The method of claim 1 wherein the first set of medical records is a multi-portion medical record and the first access key provides access to one or more portions of the first set of medical records.

11. The method of claim 1 wherein the second set of medical records is a multi-portion medical record and the second access key provides access to one or more portions of the second set of medical records.

12. The method of claim 1 further comprising:
granting said medical service provider secure access to said key organization system, wherein said access allows said medical service provider to select a patient from a group of patients associated with said medical service provider.

13. The method of claim 12 further comprising:
receiving, by said key organization system, said selection, wherein said selection is a request to access said first set of medical records;
retrieving from said centralized key repository, by said key organization system in response to said selection, said first access key; and
using, by said key organization system, said first access key to control said medical services provider's access to said first set of medical records.

14. A key distribution method comprising:
receiving, by the key organization system from a first patient using a client computer, a first access key that grants, to a medical service provider, a patient-defined level of access to a first set of medical records;
receiving, by the key organization system from a second patient using a second client computer, a second access key that grants, to said medical service provider, a patient-defined level of access to a second set of medical records; and associating, by said key organization system, said first and second access keys to said medical service provider;
storing, by said key organization system, the first and second access keys and said association in a centralized key repository; and
receiving, by said key organization system, a request from said medical service provider to access said first or second set of medical records and, responsive to said request, controlling access to said requested set of medical records using said first or second access key, wherein input of said first or second access key from said medical service provider is not required by said key organization system.

15. The method of claim 14 further comprising controlling, by said key organization system, said medical service provider's access to the first set of medical records by receiving input from said medical service provider for selecting, from a list of patients for whom access keys are associated with said medical service provider, a corresponding patient to whom the first set of medical records pertains.

16. The method of claim 14 further comprising controlling, by said key organization system, said medical service provider's access to the second set of medical records by receiving input from said medical service provider for selecting, from a list of patients for whom access keys are associated with said medical service provider, a corresponding patient to whom the second set of medical records pertains.

17. The method of claim 14 further comprising storing the first and second medical records on a centralized medical record repository.

18. The method of claim 17 wherein the centralized medical record repository and centralized key repository reside on and are accessible through said key organization system connected to a distributed computing network.

19. The method of claim 14 wherein the first set of medical records is a multi-portion medical record and the first access key provides access to one or more portions of the first set of medical records.

20. The method of claim 14 wherein the second set of medical records is a multi-portion medical record and the second access key provides access to one or more portions of the second set of medical records.

21. A key organization method comprising:
maintaining, on a remote server, a centralized key repository and a centralized medical record repository;
storing a plurality of patient medical records on the centralized medical record repository, wherein said plurality of patient medical records comprise at least of a first set of medical records containing medical information pertaining a first patient and a second set of medical records containing medical information pertaining a second patient;
storing, in said centralized key repository, a plurality of access keys that each grant patient-defined access rights to a corresponding patient's set of medical records; and
responsive to a request received from a medical service provider to access one of said sets of medical records, retrieving, by a key organization system, from said centralized key repository a determined one of said access keys that is associated with said medical service provider and which corresponds to said requested set of medical records, and controlling, by said key organization system, access by said medical service provider to said requested set of medical records using the retrieved access key.

22. The method of claim 21 further comprising:
  receiving from said first patient, a first access key, of said plurality of access keys, that grants to said medical service provider a patient-defined level of access to the first set of medical records; and
  receiving, from said second patient, a second access key, of said plurality of access keys, that grants to said medical service provider a patient-defined level of access to the second set of medical records.

23. The method of claim 22 further comprising storing, by said key organization system, the first and second access keys in the centralized key repository.

24. The method of claim 21 further comprising accessing, by said key organization system, the first set of medical records using the first access key.

25. The method of claim 21 further comprising accessing, by said key organization system, the second set of medical records using the second access key.

26. The method of claim 21 wherein the centralized medical record repository and centralized key repository reside on a remote server connected to a distributed computing network and are communicatively coupled to said key organization system.

27. The method of claim 26 wherein:
  the remote server is a web server; and
  the distributed computing network is the Internet.

28. The method of claim 21 wherein the first set of medical records is a multi-portion medical record and the first access key provides access to one or more portions of the first set of medical records.

29. The method of claim 21 wherein the second set of medical records is a multi-portion medical record and the second access key provides access to one or more portions of the second set of medical records.

30. A key organization system comprising:
  a server system including a computer processor and associated memory, the server system having a centralized key repository and a centralized medical record repository;
  wherein the server system is configured to:
  store a first set of medical records and a second set of medical records on the centralized medical record repository;
  receive a first access key associated with a medical service provider that grants to said medical service provider a patient-defined level of access to the first set of medical records;
  receive a second access key associated with said medical service provider that grants to said medical service provider a patient-defined level of access to the second set of medical records; and
  store the first access key and the second access key on the centralized key repository; and
  wherein the key organization system is configured to, responsive to receipt of a request from the medical service provider to access one of said first and second set of medical records, retrieve a determined one of the first and second access keys from the centralized key repository and use the retrieved access key to control access by said medical service provider to said requested set of medical records.

31. The system of claim 30 further comprising a client system including a computer processor and associated memory, the client system being configured to:
  communicate said request from said medical service provider to said key organization system via a communication network.

32. The system of claim 31 wherein the server system and the client system are coupled via a distributed computing network.

33. The system of claim 32 wherein the distributed computing network is the Internet.

34. The system of claim 30 wherein the first set of medical records is a multi-portion medical record and the first access key provides access to one or more portions of the first set of medical records.

35. The method of claim 30 wherein the second set of medical records is a multi-portion medical record and the second access key provides access to one or more portions of the second set of medical records.

36. A computer program product residing on a computer readable medium having a plurality of instructions stored thereon which, when executed by the processor, cause a key organization system to:
  receive, at said key organization system, a first access key that grants to a first medical service provider a first patient-defined level of access to a first set of medical records of a corresponding patient;
  receive, at said key organization system, a second access key that grants to a second medical service provider a second patient-defined level of access to said first set of medical records of said corresponding patient;
  store the first and second access keys in a centralized key repository; and
  responsive to a request received from one of said first and second medical service providers to access said first set of medical records, retrieve from said centralized key repository a determined one of said access keys that is associated with said requesting medical service provider, and using the retrieved access key to grant to the requesting medical service provider the corresponding patient-defined level of access to said first set of medical records.

37. A computer program product residing on a computer readable medium having a plurality of instructions stored thereon which, when executed by the processor, cause a key organization system to:
  receive, from a patient at a key organization system, a first access key associated with a first medical service provider that grants to said first medical service provider a first patient-defined level of access to a first set of medical records;
  receive, from said patient at said key organization system, a second access key associated with a second medical service provider that grants to said second medical service provider a second patient-defined level of access to said first set of medical records;
  store the first and second access keys in a centralized key repository;
  receive a request from said first medical service provider to access said first set of medical records; and
  retrieve, responsive to said request, said first access key from said centralized key repository to provide said first medical service provider with access to said first set of medical records wherein input of said first access key from said first medical service provider is not required by said key organization system.

38. A computer program product residing on a computer readable medium that is communicatively coupled to a server having a plurality of instructions stored thereon which, when executed by a processor of the server cause a key organization system to:
  store a plurality of patient-associated medical records on a centralized medical record repository, wherein said plurality of patient-associated medical records comprise at least of a first set of medical records associated with a first patient and a second set of medical records associated with a second patient;

store a provider-associated access keys on a centralized key repository wherein said plurality of provider-associated access keys comprise a first access key that grants a patient-defined level of access to the first set of medical records and a second access key that grants a patient-defined level of access to the second set of medical records;

responsive to a received request from a provider to access one of said first and second sets of medical records, retrieve from said centralized key repository a respective one of said first and second access keys that grants the requesting provider a patient-defined level of access to the requested one of said first and second sets of medical records; and use said retrieved access key to grant said requesting provider the corresponding patient-defined level of access to the requested one of said first and second sets of medical records.

39. The method of claim 12 wherein said secure access is granted after said medical service provider passes a security test issued by said key organization system.

* * * * *